(12) United States Patent
Pillai et al.

(10) Patent No.: US 8,983,605 B2
(45) Date of Patent: Mar. 17, 2015

(54) SYSTEM AND METHOD FOR DETECTING PULMONARY EDEMA BASED ON IMPEDANCE MEASURED USING AN IMPLANTABLE MEDICAL DEVICE DURING A LEAD MATURATION INTERVAL

(71) Applicant: Pacesetter, Inc., Sunnyvale, CA (US)

(72) Inventors: Ajit Pillai, Sunnyvale, CA (US); Cecilia Qin Xi, San Jose, CA (US)

(73) Assignee: Pacesetter, Inc, Sunnyvale, CA (US)

( * ) Notice: Subject to any disclaimer, the term of this patent is extended or adjusted under 35 U.S.C. 154(b) by 0 days.

(21) Appl. No.: 13/903,846

(22) Filed: May 28, 2013

(65) Prior Publication Data

US 2013/0261492 A1    Oct. 3, 2013

Related U.S. Application Data

(62) Division of application No. 12/474,157, filed on May 28, 2009, now Pat. No. 8,473,054.

(51) Int. Cl.
*A61N 1/362*     (2006.01)
*A61N 1/365*     (2006.01)
(Continued)

(52) U.S. Cl.
CPC ............ *A61B 5/0538* (2013.01); *A61N 1/3627* (2013.01); *A61N 1/36521* (2013.01); *A61N 1/3702* (2013.01)
USPC .................. 607/28; 607/17; 607/27; 607/116; 600/547

(58) Field of Classification Search
USPC .................... 607/17, 27, 28, 116; 600/547
See application file for complete search history.

(56) References Cited

U.S. PATENT DOCUMENTS

| 5,328,460 | A | 7/1994 | Lord et al. ...................... 604/67 |
| 5,957,861 | A | 9/1999 | Combs et al. ................. 600/547 |

(Continued)

FOREIGN PATENT DOCUMENTS

| EP | 1 911 399 | 10/2007 |
| WO | WO 2009/005559 | 1/2009 |

OTHER PUBLICATIONS

U.S. Appl. No. 12/474,157, Notice of Allowance mailed Mar. 28, 2013.

(Continued)

*Primary Examiner* — Niketa Patel
*Assistant Examiner* — Christopher A Flory
(74) *Attorney, Agent, or Firm* — Theresa A. Raymer

(57) ABSTRACT

Techniques are provided for use by implantable medical devices such as cardiac resynchronization therapy (CRT) devices for detecting pulmonary edema based on transthoracic impedance sensed using cardiac pacing/sensing leads, wherein detection can be performed while lead maturation occurs. Briefly, the implantable device determines whether the leads are within an initial post-implant interval following implant during which lead maturation generally occurs. The device then detects pulmonary edema or related medical conditions within the patient based on transthoracic impedance using a set of detection parameters adjusted for use during the post-implant interval. Thus, rather than "blanking" impedance data during lead maturation, the device instead detects and processes impedance during this period to identify possible episodes of pulmonary edema so that appropriate measures can be undertaken, such as delivery of warnings or titration of appropriate medications.

20 Claims, 9 Drawing Sheets

(51) Int. Cl.
*A61N 1/37* (2006.01)
*A61B 5/053* (2006.01)

(56) References Cited

U.S. PATENT DOCUMENTS

| | | | | |
|---|---|---|---|---|
| 6,129,746 | A * | 10/2000 | Levine et al. | 607/27 |
| 6,366,812 | B1 * | 4/2002 | Levine et al. | 607/27 |
| 6,512,952 | B2 | 1/2003 | Stahmann et al. | 607/9 |
| 6,622,045 | B2 | 9/2003 | Snell et al. | 607/30 |
| 6,628,988 | B2 | 9/2003 | Kramer et al. | 607/9 |
| 6,643,546 | B2 | 11/2003 | Mathis et al. | 607/9 |
| 7,010,347 | B2 | 3/2006 | Schechter | 607/17 |
| 7,065,400 | B2 | 6/2006 | Schechter | 607/2 |
| 7,283,871 | B1 * | 10/2007 | Hofstadter et al. | 607/5 |
| 7,398,122 | B1 * | 7/2008 | Hofstadter et al. | 607/8 |
| 7,447,543 | B2 | 11/2008 | Belalcazar et al. | 600/547 |
| 7,848,806 | B1 * | 12/2010 | Kroll | 607/8 |
| 8,060,200 | B2 * | 11/2011 | Hofstadter et al. | 607/8 |
| 2006/0041280 | A1 | 2/2006 | Stahmann et al. | 607/17 |
| 2006/0224190 | A1 * | 10/2006 | Gill et al. | 607/3 |
| 2006/0258952 | A1 | 11/2006 | Stahmann et al. | 600/547 |
| 2006/0293609 | A1 | 12/2006 | Stahmann et al. | 600/547 |
| 2007/0179390 | A1 | 8/2007 | Schecter | 600/508 |
| 2008/0243025 | A1 | 10/2008 | Holmstrom et al. | 600/547 |
| 2008/0306567 | A1 | 12/2008 | Park et al. | 607/27 |
| 2009/0216145 | A1 * | 8/2009 | Skerl et al. | 600/533 |
| 2010/0305641 | A1 * | 12/2010 | Pillai et al. | 607/17 |

OTHER PUBLICATIONS

U.S. Appl. No. 12/474,157, Final Office Action mailed Dec. 17, 2012.
U.S. Appl. No. 12/474,157, Non-final Office Action mailed Jul. 18, 2012.

* cited by examiner

SYSTEM AND METHOD FOR DETECTING PULMONARY EDEMA BASED ON IMPEDANCE MEASURED USING AN IMPLANTABLE MEDICAL DEVICE DURING A LEAD MATURATION INTERVAL

PRIORITY CLAIM

This application is a Divisional of U.S. patent application Ser. No. 12/474,157, filed May 28, 2009, which is entitled "System and Method for Detecting Pulmonary Edema Based on Impedance Measured Using an Implantable Medical Device During a Lead Maturation Interval," now U.S. Pat. No. 8,473,054, incorporated herein by reference in its entirety.

FIELD OF THE INVENTION

The invention generally relates to implantable medical devices, such as pacemakers, implantable cardioverter/defibrillators (ICDs) or cardiac resynchronization therapy (CRT) devices, and in particular to techniques for detecting and tracking heart failure or pulmonary edema using such devices.

BACKGROUND OF THE INVENTION

Heart failure is a debilitating disease in which abnormal function of the heart leads in the direction of inadequate blood flow to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles (particularly the left ventricle) to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

Pulmonary edema (PE) is a swelling and/or fluid accumulation in the lungs often caused by heart failure. Briefly, the poor cardiac function resulting from heart failure can cause blood to back up in the lungs, thereby increasing blood pressure in the lungs, particularly pulmonary venous pressure. The increased pressure pushes fluid—but not blood cells—out of the blood vessels and into lung tissue and air sacs (i.e. the alveoli). This can cause severe respiratory problems and, left untreated, can be fatal, PE can also arise due to other factors besides heart failure, such as infections.

In view of the potential severity of PE, it is highly desirable to detect the condition so that appropriate therapy can be provided. Many patients susceptible to PE are candidates for pacemakers, ICDs, CRT devices or CRT-D devices. A CRT-D is a cardiac resynchronization therapy device with defibrillation capability. Briefly, CRT seeks to normalize asynchronous cardiac electrical activation and resultant asynchronous contractions associated with CHF by delivering appropriate pacing stimulus to both ventricles. The stimulus can be synchronized or otherwise controlled so as to improve overall cardiac function. This may have the additional beneficial effect of reducing the susceptibility to life-threatening tachyarrhythmias.

CRT and related therapies are discussed in, for example, U.S. Pat. No. 6,643,546 to Mathis, et al., entitled "Multi-Electrode Apparatus and Method for Treatment of Congestive Heart Failure"; U.S. Pat. No. 6,628,988 to Kramer, et al., entitled "Apparatus and Method for Reversal of Myocardial Remodeling with Electrical Stimulation"; and U.S. Pat. No. 6,512,952 to Stahmann, et al., entitled "Method and Apparatus for Maintaining Synchronized Pacing". See, also, U.S. Pat. No. 7,065,400 of Schechter, entitled "Method and Apparatus for Automatically Programming CRT Devices"; U.S. Pat. No. 7,010,347 of Schechter, entitled "Optimization of Impedance Signals for Closed Loop Programming of Cardiac Resynchronization Therapy Devices"; U.S. Patent Application No. 2008/0306567 of Park et al., entitled "System and Method for Improving CRT Response and Identifying Potential Non-Responders to CRT Therapy"; and U.S. Patent Application No. 2007/0179390 of Schecter, entitled "Global Cardiac Performance."

Accordingly, it is desirable to provide such devices with the capability to automatically detect and respond to PE. Aspects of the present invention are primarily directed to this end.

One technique for detecting PE uses transthoracic electrical impedance signals measured using leads of the device to detect a pulmonary "fluid overload," i.e. a significant increase in pulmonary fluids. In this regard, a significant drop in transthoracic impedance is deemed to be indicative of such a fluid overload. In response, diuretics such as furosemide or bumetanide can be administered to the patient to reduce the fluid overload. (Diuretics are drugs that increase the flow of urine, thus eliminating water from the body, ultimately reducing pulmonary fluid levels.)

The use of impedance is promising since transthoracic impedance can be readily measured in situ using pacemakers, ICDs, CRTs, or CRT-Ds and their leads. However, a significant concern with impedance-based techniques is that such techniques typically cannot be used during an initial lead maturation interval following lead/device implant (also referred to as a lead stabilization phase.) Briefly, to detect PE using transthoracic impedance, as well as to provide for routine cardiac pacing/sensing functions, a set of leads is implanted in the heart. Each lead includes one or more electrodes. Impedance pulses are delivered between the electrodes and the device housing through at least a portion of lung tissue to measure impedance values representative of the amount of fluid within the lungs.

However, during a lead maturation period of about one month following lead implant, the impedance values detected using the leads are deemed to be unreliable because of transient changes in tissues adjacent the leads. For example, fibrous tissue often grows in and around the area of implantation, which can affect the impedance values measured using the leads. As such, impedance measurements made by the implanted device can vary over time as tissue growth occurs, resulting in changes in impedance not due to changes in actual fluid levels.

Typically, therefore, impedance-based PE detection techniques are not activated until completion of a waiting period that is at least as long as the lead maturation period. (The waiting period is typically about two weeks longer than the lead maturation period to permit the device to collect sufficient impedance data following lead maturation to make a reliable detection of PE. That is, the waiting period is typically at least six weeks.) Moreover, with many predecessor techniques, no impedance data is even collected during the initial lead maturation period, i.e. the data is "blanked."

However, it has been found that heart failure exacerbation events (which trigger episodes of PE) can occur during the waiting period. Hence, it would be highly desirable to provide improved techniques to permit transthoracic impedance to be reliably detected during the waiting period and the present invention is primarily directed to this end.

SUMMARY OF THE INVENTION

In accordance with the invention, techniques are provided for use by implantable medical devices for detecting medical conditions such as PE based on transthoracic impedance, wherein detection can be performed during a post-implant lead maturation waiting period. In the following, this "waiting period" is instead referred to as a "post-implant interval," since waiting is no longer required. Briefly, the implantable device determines whether the lead is within an initial post-implant interval following lead implant during which lead maturation occurs. The device then detects PE or related cardiopulmonary conditions within the patient based on transthoracic impedance using a set of detection parameters adjusted for use during the post-implant interval. Thus, rather than "blanking" impedance data during lead maturation, as with the predecessor techniques discussed above, the device instead detects impedance data during lead maturation to identify possible episodes of PE or other cardiopulmonary conditions such as heart failure.

In an exemplary embodiment, where the implantable device is a CRT-D, an impedance-based PE detection system within the CRT-D is promptly activated following implant of the device and its leads into a patient. Upon activation, the detection system retrieves a set of pre-programmed PE detection parameters intended for use following lead maturation. These may be referred to as the "standard" PE detection parameters. Exemplary detection parameters include: a long-term average window duration, a short-term average window duration and a PE detection threshold.

The PE detection system then determines the duration of the post-implant interval for use in determining whether to adjust the detection parameters. In one example, the post-implant interval is set equal to a pre-programmed lead maturation period (during which lead maturation actually occurs) plus the duration of the long-term average window. For example, if the pre-programmed lead maturation period is one month and the long-term average window duration is two weeks, then the post-implant interval is therefore set to six weeks. (This interval can have the same duration as predecessor waiting periods, although, as noted, waiting is no longer required during the interval.) Then, if the leads are still within the initial post-implant interval, the system adjusts the PE detection parameters based on the amount of time since implant to compensate for on-going lead maturation. If the leads are beyond the initial post-implant interval, the system instead uses non-adjusted PE detection parameters (i.e. the system uses the standard parameters initially retrieved.)

In an illustrative embodiment, during the initial post-implant interval, the system selectively reduces both the PE detection threshold and the duration of the long-term averaging window. In one particular example, the PE threshold is set to a fraction of its standard value, with the fractional amount varying during the post-implant interval based on the amount of time since implant (such as to $\frac{1}{6}$, $\frac{1}{3}$, $\frac{1}{2}$, $\frac{2}{3}$ or $\frac{5}{6}$ of its standard value.) That is, during a first portion of the post-implant interval, the threshold is set to $\frac{1}{6}$ of its standard value. During a next portion, the threshold is increased to $\frac{1}{3}$ of its standard value. By the end of the post-implant interval, the threshold is back to its standard value. Thereafter, no further changes are made to the threshold (unless the leads need to be re-implanted.)

Likewise, in the illustrative embodiment, the long-term window duration is set to a fraction of its standard value during the post-implant interval, with the fractional amount increasing based on the amount of time since implant (such as to $\frac{1}{4}$, $\frac{1}{2}$, or $\frac{3}{4}$ of its standard value) so that, by the end of the interval, the duration is back to its standard value. Thereafter, no further changes are made to the long-term window duration (unless the leads need to be re-implanted.)

Alternatively, various other linear or non-linear adjustment functions may be used to adjust the detection parameters during the interval. Also, depending upon the programming of the device, other detection parameters can be adjusted during the interval. In some cases, e.g., it might be appropriate to also adjust the duration of the short-term window. In general, any of the detection parameters applied by the device to transthoracic impedance signals can be adjusted during the post-implant interval to permit detection of medical conditions.

System and method implementations are described herein.

BRIEF DESCRIPTION OF THE DRAWINGS

The above and further features, advantages and benefits of the invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
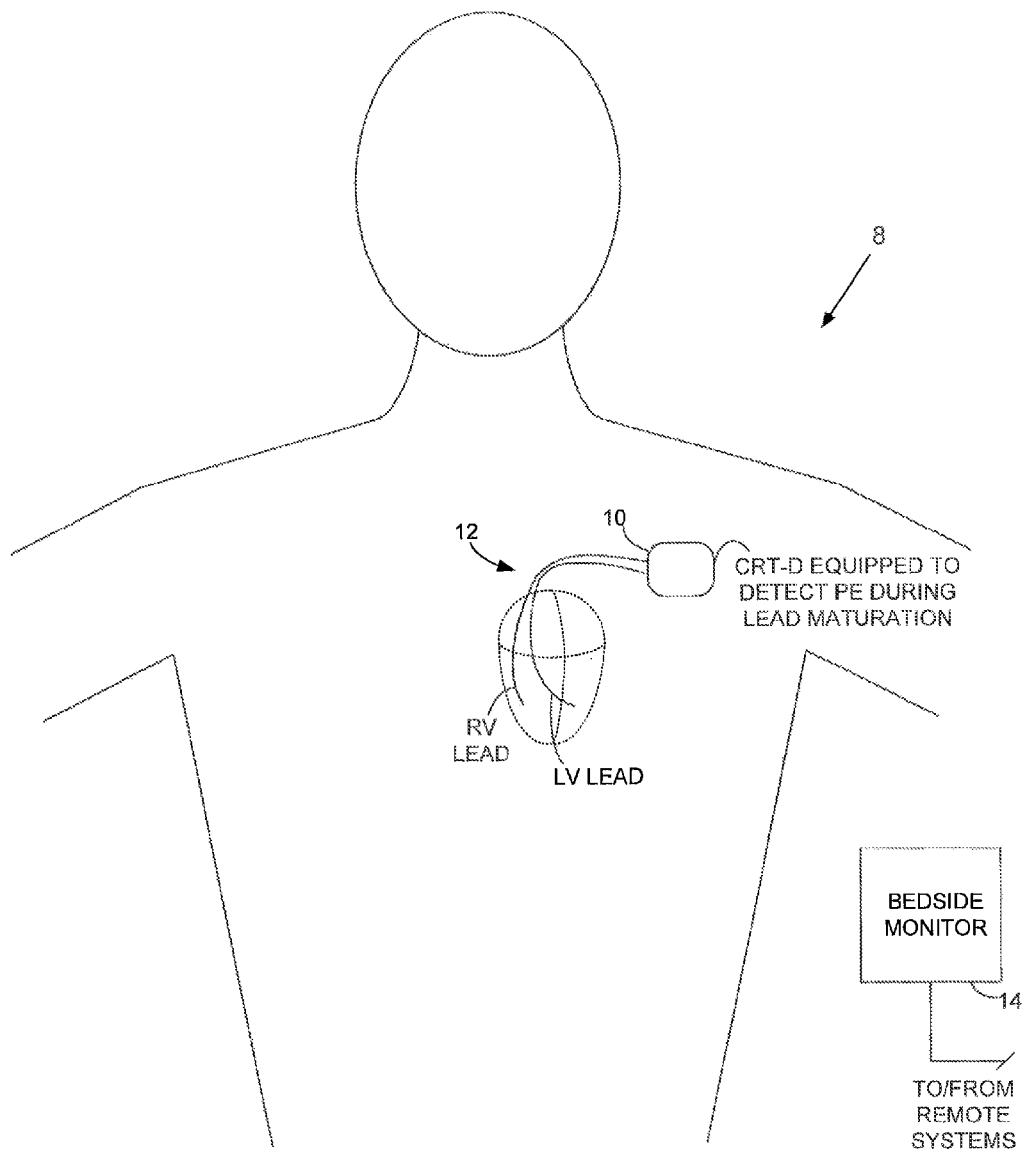
FIG. 1 illustrates pertinent components of an implantable medical system having a CRT-D, pacemaker or ICD capable of monitoring for PE based on transthoracic impedance during an initial post-implant interval (as well as after the initial interval has elapsed)

FIG. 1 illustrates an implantable medical system 8 capable of monitoring for PE or related cardiopulmonary conditions based on transthoracic impedance (or similar electrical parameters.) In particular, the implantable system is equipped to detect PE during an initial post-implant interval during which lead maturation occurs, as well as after the interval has completed. To this end, medical system 8 includes a CRT-D 10 or other cardiac rhythm management device capable of applying impedance detection pulses to patient thoracic tissues via one or more cardiac sensing/pacing leads 12 implanted within the heart of the patient. Transthoracic impedance is measured by CRT-D 10 based on the impedance detection pulses. (In FIG. 1, two exemplary leads are shown—an RV lead and an LV lead—in stylized form. A more complete set of leads is set forth in FIG. 8.)

The CRT-D then tracks impedance to detect PE using index-based detection techniques to be described in detail below, wherein PE detection parameters are adjusted depending on whether the leads are in the post-implant interval. Upon detection of PE, warning signals may be generated using a bedside monitor 14, a hand-held personal advisory module (PAM), not separately shown, an internal warning device provided within the CRT-D or to any other suitable device such as an ICD-supported mobile phone (e.g. Merlin Mobile™.) The bedside monitor or PAM can provide audible or visual alarm signals to alert the patient or caregiver, as well as any appropriate textual or graphic displays. The internal warning device (see FIG. 9) may be a vibrating device or a "tickle" voltage device that, in either case, provides perceptible stimulation to the patient to alert the patient.

The bedside monitor may be directly networked with a centralized computing system for immediately notifying a physician or other caregiver of any concerns. The centralized system may include such systems as the HouseCall™ system or the Merlin@home/Merlin.Net systems of St. Jude Medical. A system incorporating bedside monitoring units connected to a centralized external programmer system is described in U.S. Pat. No. 6,622,045 to Snell et al., "System and Method for Remote Programming of Implantable Cardiac Stimulation Devices."

In some implementations, the CRT-D may also be equipped to titrate diuretics or other medications in response to PE. For example, although not specifically shown in FIG. 1, the implantable system can be equipped with a subcutaneous drug pump or other implantable drug dispensation device capable of the delivering medications directly to patient tissues. Implantable drug pumps for use in dispensing medications are discussed in U.S. Pat. No. 5,328,460 to Lord, et al., entitled "Implantable Medication Infusion Pump Including Self-Contained Acoustic Fault Detection Apparatus." (This patent also discusses implantable "tickle" warning devices that may be used to deliver warning signals.) In other embodiments, information regarding dosages of medications to be taken by the patient is instead transmitted to the bedside monitor 14 or PAM, which generates diagnostic displays instructing the patient to take certain dosages of diuretics or other medications.

In addition, diagnostic information pertaining to changes in transthoracic impedance, and to any medical conditions detected therefrom, may be stored within the CRT-D for subsequent transmission to an external programmer (see FIG. 9) for review by a physician during a follow-up session between patient and physician. The physician then prescribes any appropriate therapies. The physician may also adjust the operation of the CRT-D to activate, deactivate or otherwise control any therapies that are automatically delivered by the device.

Additionally, the CRT-D performs a wide variety of pacing and/or defibrillation functions such as delivering pacing pulses is response to an arrhythmia or generating or delivering defibrillation shocks in response to cardiac fibrillation.

Figure 2:
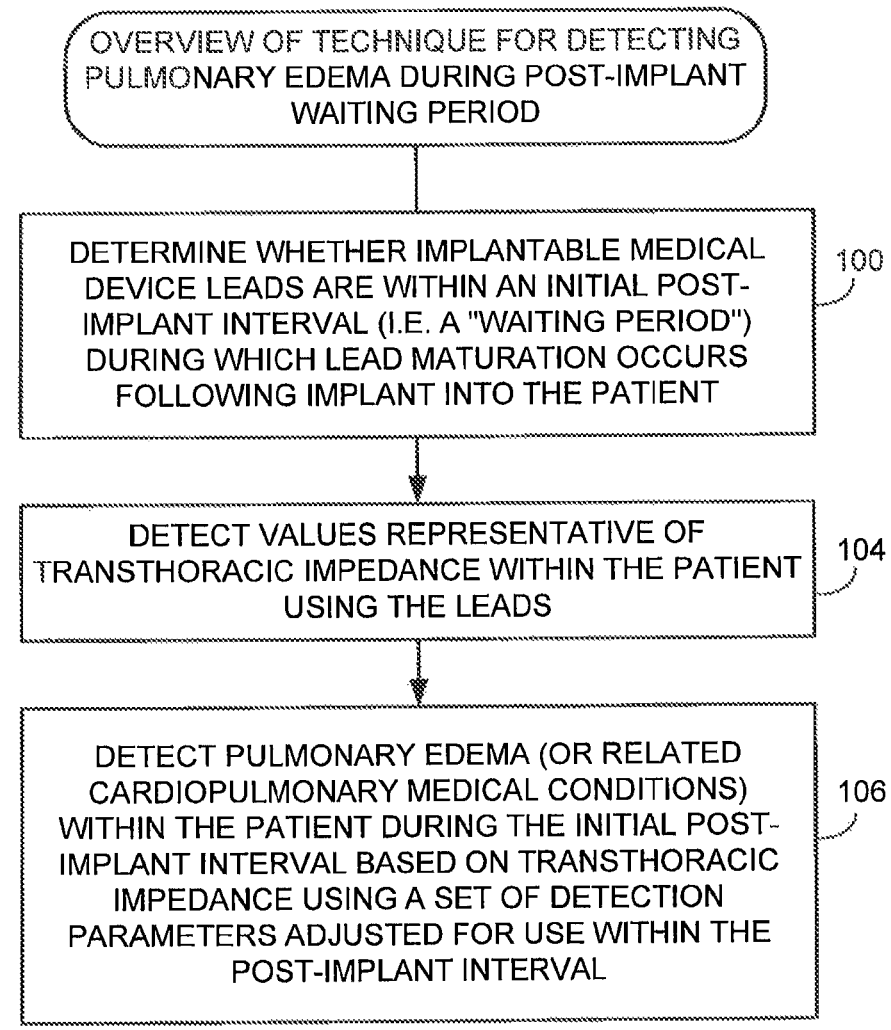
FIG. 2 is a flowchart providing an overview of the post-implant PE monitoring technique performed by the system of FIG. 1.

FIG. 2 broadly summarizes the general technique for monitoring transthoracic impedance to detect PE during the post-implant interval, which is employed by the system of FIG. 1 or other suitably equipped systems. Beginning at step 100, the CRT-D determines whether the leads of the CRT-D are within the initial post-implant interval following lead implantation. The interval is programmable. In one example, the interval includes a one month lead maturation period (during which lead maturation actually occurs) and a subsequent two week long-term averaging period, for an overall interval of six weeks. The determination of whether the leads are within this interval can be made based on an internal clock within the CRT-D, which is activated upon implant.

At step 102, the CRT-D detects transthoracic impedance based on impedance detection pulses delivered between, e.g., an LV ring (LVr) electrode and a device housing/case electrode such that the impedance detection vector passes through at least a portion of the lung.

(Combinations of vectors can be used. A preferred vector is a combination of RVcoil-Case and LVring-Case.)

At step 104, the CRT-D then detects PE (or other related cardiopulmonary conditions such as heart failure exacerbation events) within the patient based on the transthoracic impedance signals using a set of detection parameters that are adjusted for use within the initial post-implant interval. As noted above, the detection parameters can include a long-term average window duration, a short-term average window duration and a PE detection threshold, one or more of which is adjusted by the CRT-D if the lead is within the initial post-implant interval. Exemplary techniques for making the adjustments are set forth below. After the initial post-implant interval is complete, the device uses non-adjusted versions of the detection parameters.

Hence, FIGS. 1 and 2 provide an overview of an implantable system capable of monitoring changes in transthoracic impedance—including changes occurring during the initial post-implant interval—and further capable of detecting PE based on transthoracic impedance, delivering appropriate warnings, titrating medication dosages or controlling other forms of therapy, if needed. Embodiments may be implemented that do not necessarily perform all of these functions. For example, embodiments may be implemented that only provide, for example, for tracking PE and generating warnings. Drug pumps are not necessarily implanted. Bedside monitors or RAMS are not necessarily used. Some implementations may employ some form of external device for generating warning signals but no internal warning device. These are just a few exemplary embodiments. No attempt is made herein to describe all possible combinations of components that may be provided in accordance with the general principles of the invention.

Also, note that, the particular shapes, sizes and locations of the implanted components shown in FIG. 1 are merely illustrative and may not necessarily correspond to actual implant locations. Preferred implant locations for the leads are more precisely illustrated in FIG. 8.

Exemplary Impedance-based Techniques for Detecting PE

FIGS. 3-7 illustrate an exemplary technique for detecting PE within a patient including PE episodes occurring during the initial lead maturation interval. Beginning at step 200 of FIG. 3, the CRT-D and its leads are implanted within the patient and impedance-based PE detection is enabled. That is, PE detection is enabled within the CRT-D without first waiting for completion of any lead maturation-based waiting period.

At step 202, the CRT-D inputs or retrieves from memory a set of standard PE detection parameters intended for use following lead maturation including the aforementioned: long-term average window duration, short-term average window duration and PE detection threshold. (Note that, in some examples, PE detection includes an additional parameter that specifies the hours needed to reset the fluid index. However, in the preferred embodiment, this parameter is not adjusted based on lead maturation.) These are the parameters to be used by the device once the post-implant interval has elapsed. Exemplary values for the parameters are: two weeks for the long-term window duration; two days for the short-term duration; and fifteen units for the PE detection threshold.

Note that the choice of a particular value for use as the standard PE detection threshold depends on various factors, such as the manner by which impedance values are normalized by the CRT-D and on the particular algorithm to be used by the CRT-D to increase a PE detection index (which is compared against the threshold to actually detect PE.) In the present example, the CRT-D is programmed to determine whether a long-term average (of normalized impedance values) is greater than the short-term average (of normalized impedance values) and, if so, the CRT-D increases a PE detection index by the difference between the values. (See, step 220, discussed below). As can be appreciated, the relative different between these values depends in part on the normalization of the impedance values.

In the present example, it is assumed that the various factors affecting the choice of the standard detection threshold are programmed such that a PE detection threshold of fifteen accumulated difference units is appropriate for detecting PE within a patient after the post-implant interval has elapsed. Otherwise routine experimentation can be performed to identify preferred or optimal values for use as the PE detection threshold depending on variations in these and other factors, such as variations in the frequency by which the PE index is accumulated.

Also, at step 202, the CRT-D can input or retrieve a value specifying the expected duration of the lead maturation period. This is usually set to one month, though. Hence, a lead maturation period of one month is merely an illustrative example. Also, it should be understood that other sets of detection parameters might be specified depending upon the programming of the particular device. For example, the device might be designed to distinguish the severity of different heart failure events. At step 204, the CRT-D sets the post-implant interval equal to the lead maturation period plus the long-term average window duration retrieved at step 202. Assuming that the lead maturation period is one month and the long-term window duration is two-weeks, the overall interval is thereby set to six weeks. Then, beginning at step 206, the CRT-D tracks the amount of time since implant using its internal clock to determine whether the leads are within the initial interval. Assuming that the leads are within the interval, then, at step 208, the CRT-D adjusts the PE detection parameters based on the amount of time since implant to, e.g., vary the long-term window duration and/or the PE threshold.

Figure 4:
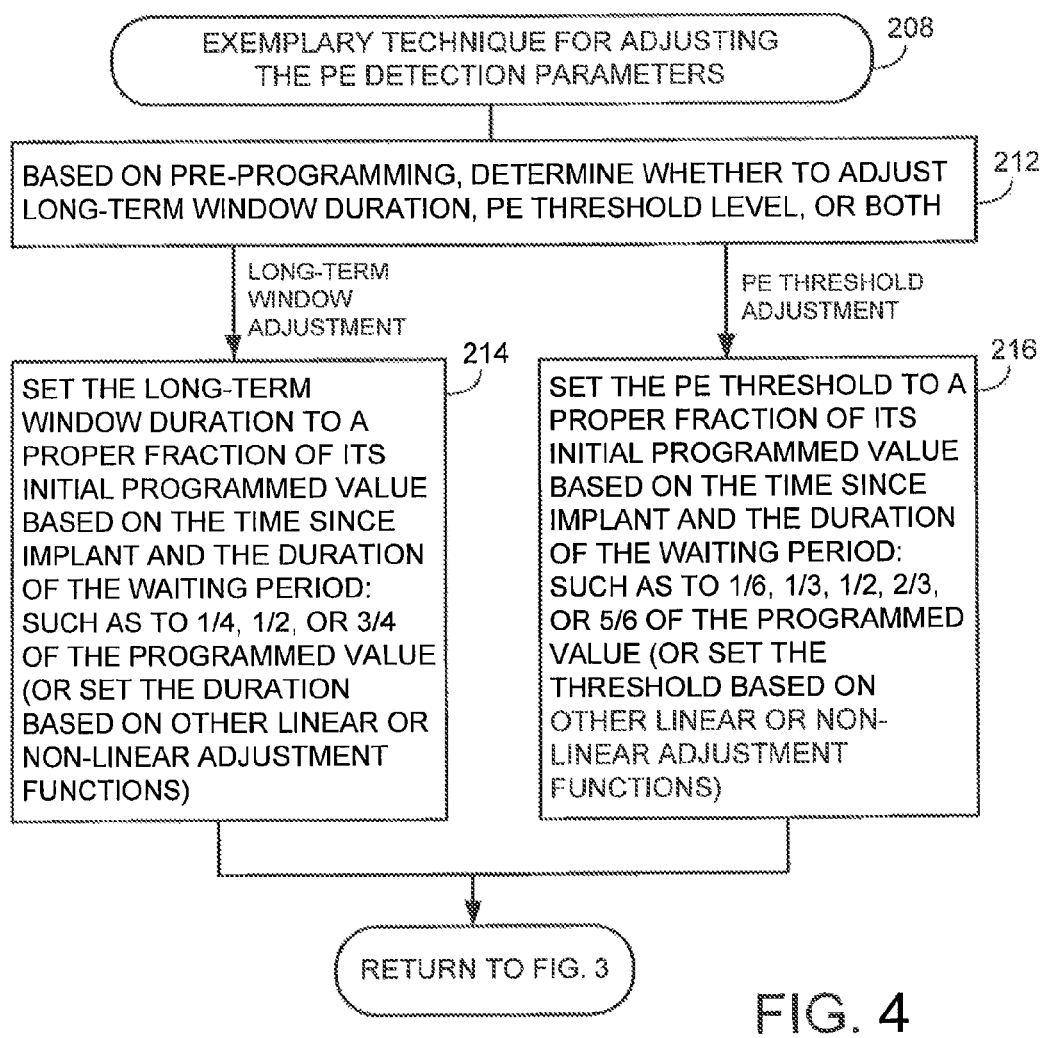
FIG. 4 illustrates an exemplary technique for adjusting PE detection parameters (including a long-term averaging window and a PE detection threshold) based on the amount of time since lead implant, in accordance with the technique of FIG. 3.

FIG. 4 illustrates an exemplary procedure for adjusting the PE detection parameters. Based on device pre-programming, at step 212, the CRT-D determines whether to adjust the long-term window duration, the PE threshold level, or both. This decision may be programmed into the device by the clinician or otherwise pre-specified. In other examples, other detection parameters might be selected for adjustment as well.

If the long-term window is to be adjusted during the post-implant interval, then, at step 214, the CRT-D sets the duration of the long-term window to a proper fraction of its initial programmed value (i.e. a fraction of the value retrieved at step 202) based on the amount of time since lead implant and the overall duration of the post-implant interval (determined at step 204). For example, the long-term window duration can be set to ¼, ½, or ¾ of the standard value, i.e. step-wise adjustments can be made. In one specific embodiment, the port-implant interval is divided into three equal sub-intervals. During the first sub-interval, the long-term window duration is set to ¼ of its standard duration. So, if the standard duration is two weeks, the long-term window duration is set to only 3.5 days during this first sub-interval. During the second sub-interval, the long-term window duration is increased to 7 days. During the third sub-interval, the long-term window duration is increased to 10.5 days. (Ultimately, once the entire post-implant interval is complete, the long-term window duration is increased to fourteen days, i.e. it is returned to its standard value.)

Alternatively, at step 214, the long-term window duration can be adjusted based on a linear adjustment function, such that the duration changes gradually from an initial starting value (e.g. 3.5 days) to its final standard value (e.g. fourteen days). Non-linear adjustment functions can instead be used. Otherwise routine experimentation can be performed to identify preferred or optimal adjustment functions sufficient to permit PE events to be detected during the post-implant interval without a significant number of false detections (i.e. without unduly increasing a false excursion rate (FER.))

If the PE detection threshold is to be adjusted during the post-implant interval, then, at step 216, the CRT-D sets the threshold to a proper fraction of its standard value based on the amount of time since lead implant and the overall duration of the post-implant interval. For example, the detection threshold can be set to ⅙, ⅓, ½, ⅔ or ⅚ of the standard value, i.e. step-wise adjustments can also be made. Again, the post-implant interval is divided into a set of sub-intervals (though these sub-intervals need not have the same duration as the sub-intervals for use in adjusting the long-term window.) With the standard threshold set to 15 units, the threshold for use during the first sub-interval is thereby 2.5 units. This threshold is then increased to 5.0 during the next sub-interval, and so on. As with the adjustments made to the long-term window, the adjustments to the PE threshold can be set to periodically increase the threshold until it has risen to its standard value at the end of the entire post-implant adjustment interval.

At step 216, the PE detection threshold can alternatively be set based on a linear adjustment function, such that the threshold changes gradually from an initial starting value (e.g. a value of 2.5 units) to its final standard value (e.g. a value of 15 units). Non-linear adjustment functions can instead be used. Otherwise routine experimentation can again be performed to identify preferred or optimal adjustment functions sufficient to permit PE events to be detected during the post-implant interval without an undue number of false detections.

Preferably, both the long-term window duration and the PE detection threshold are adjusted by the CRT-D, though in some implementations only one or the other is adjusted, as determined by device pre-programming. If only one or other is adjusted, a different adjustment scheme may be used that takes into account the fact that only one of these parameters is being adjusted, so as to permit PE events to be reliably detected during the post-implant interval. Again, otherwise routine experimentation can be performed to identify particular adjustment schemes.

Returning to FIG. 3, at step 218, the CRT-D then detects transthoracic impedance and calculates long-term and short-term averages based on the current window durations. Transthoracic impedance (Z) can be detected by applying impedance detection pulses between, e.g., LVr and the device housing electrode. In some examples, suitable filters may be employed to filter out cardiogenic variations in the signal (representative of the beating of the heart) and/or respiratory variations (representative of breathing) so as to leave only those portions representative of fluid accumulations within the lungs. However, in some implementations, impedance is averaged over a period of at least a couple of days (even when using the short-term window) and so, in those implementations, it is typically not necessary to filter out cardiogenic or respiratory variations.

A particularly effective tri-phasic impedance detection pulse for use in detecting impedance is described in U.S. patent application Ser. No. 11/558,194 of Panescu et al., filed Nov. 9, 2006, entitled "Closed-Loop Adaptive Adjustment of Pacing Therapy based on Cardiogenic Impedance Signals Detected by an Implantable Medical Device." However, other impedance detection pulses or waveforms may instead be exploited.

Note that, rather than detecting impedance, other related electrical signals can instead be exploited, such as admittance, conductance, immittance or their equivalents. This depends, in part, on how these parameters are defined. Impedance is the numerical reciprocal of admittance. Conductance is the numerical reciprocal of resistance. In general, impedance and admittance are vector quantities, which may be represented by complex numbers (having real and imaginary components.) The real component of impedance is resistance. The real component of admittance is conductance. When exploiting only the real components of these values, conductance can be regarded as the reciprocal of impedance. Likewise, when exploiting only the real components, admittance can be regarded as the reciprocal of resistance. Immittance represents either impedance or admittance.

Generally, herein, "values representative of impedance" broadly encompasses impedance and/or any of these electrical equivalents and those skilled in the art can readily covert one such parameter to another.

During step 218, the long-term and short-term averages are calculated simply by averaging a normalized version of the impedance signal over the long-term and short-term windows. So, if the short-term moving window is set to two days, the CRT-D averages the last two days worth of impedance data and stores that calculated value as the short-term average. If the long-term moving window is set to 3.5 days, the CRT-D averages the last 3.5 days worth of impedance data and stores that value as the long-term average. Note that, with long-term duration set to 3.5 days, the CRT-D will not begin its PE detection until 3.5 days after lead implant. This is still much sooner than predecessor techniques that wait until a six-week waiting period has elapsed. Nevertheless, to provide for still earlier PE detection (i.e. earlier than even 3.5 days following implant), the long-term window can potentially be made even shorter (as specified by the programming of step 214 of FIG. 4.) Otherwise routine experimentation can again be performed to identify the shortest possible long-term window duration that is sufficient to permit PE to be reliably detected without an undue risk of false detection. For most purposes, though, 3.5 days is sufficient. (Note also that the durations of the moving windows remain unchanged until the time is reached to adjust the long-term window duration (at step 214 of FIG. 4.)

At step 220, the CRT-D, determines whether the long-term average is greater than the short-term average and, if so, increases a PE detection index. The CRT-D then compares the index to the current value for the PE detection threshold. As such, if the detection threshold is initially set to 2.5 units following device implant, then the accumulated PE index is compared against that threshold at step 220 to detect an episode of PE. If the accumulated PE index is greater than 2.5, an episode of PE is thereby indicated. In one example, the PE detection index is increased at step 220 by the amount of the difference between the two moving averages. In a preferred example, however, the amount is instead just the duration over which the long-term average is greater than the short-term average, not the amount of the difference between the two moving averages.

Assuming PE has been detected at step 220, then the CRT-D at step 222 titrates diuretics (if an implantable/subcutaneous drug pump is provided), generate warning signals to notify clinician (via any of the aforementioned internal or external warning devices), controls other forms of therapy (such as by adjusting pacing therapy where appropriate); and records diagnostic information for clinician review. Such diagnostics can includes information pertaining to trends in transthoracic impedance, as well as tables listing the particular detection parameters in use at the time of PE detection. Also, since PE is often due to an exacerbation of heart failure, the device can generate warning signals as to heart failure, as well. In the preferred implementation, wherein the implantable medical device is a CRT or CRT-D device, CRT is controlled.

On the other hand, if PE is not indicated at step 220, then the CRT-D returns to step 206 to repeat the analysis process. As the amount of time since lead implant increases, the various PE detection parameters are periodically adjusted (via the steps of FIG. 4) such that the long-term window expands and the PE detection threshold increases. Any additional episodes of PE are thereby detected if they arise. (Note that once a given episode of PE is detected, the PE index is reset to zero.)

Eventually, the amount of time since implant will exceed the post-implant interval such that step 224 is performed where the CRT-D now calculates long-term and short-term averages based on non-adjusted window durations. That is, the standard long-term window duration originally retrieved at step 202 is now used. At step 220, the PE index is compared against the standard threshold (rather than an adjusted threshold value). Thereafter, only the standard parameters are used since the lead is now well beyond the lead maturation period. (If any of the leads used to detect transthoracic impedance need to be re-implanted, then a new lead maturation period should be tracked and the overall process repeated.)

PE Detection Examples

Figure 3:
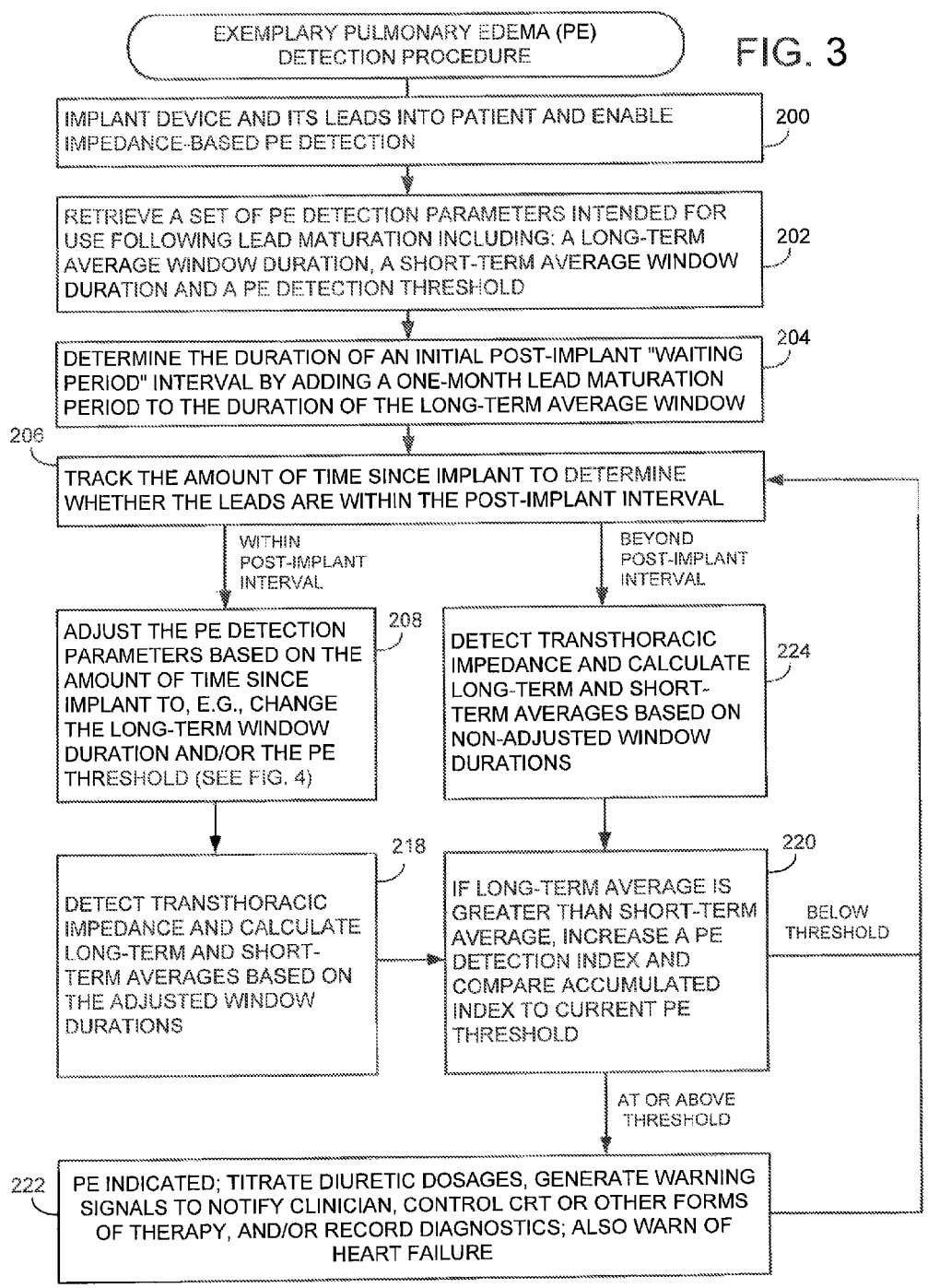
FIG. 3 illustrates an exemplary technique for detecting PE based using detection parameters adjusted based on whether the leads are within the initial post-implant interval, in accordance with the general technique of FIG. 2.
Figure 5:
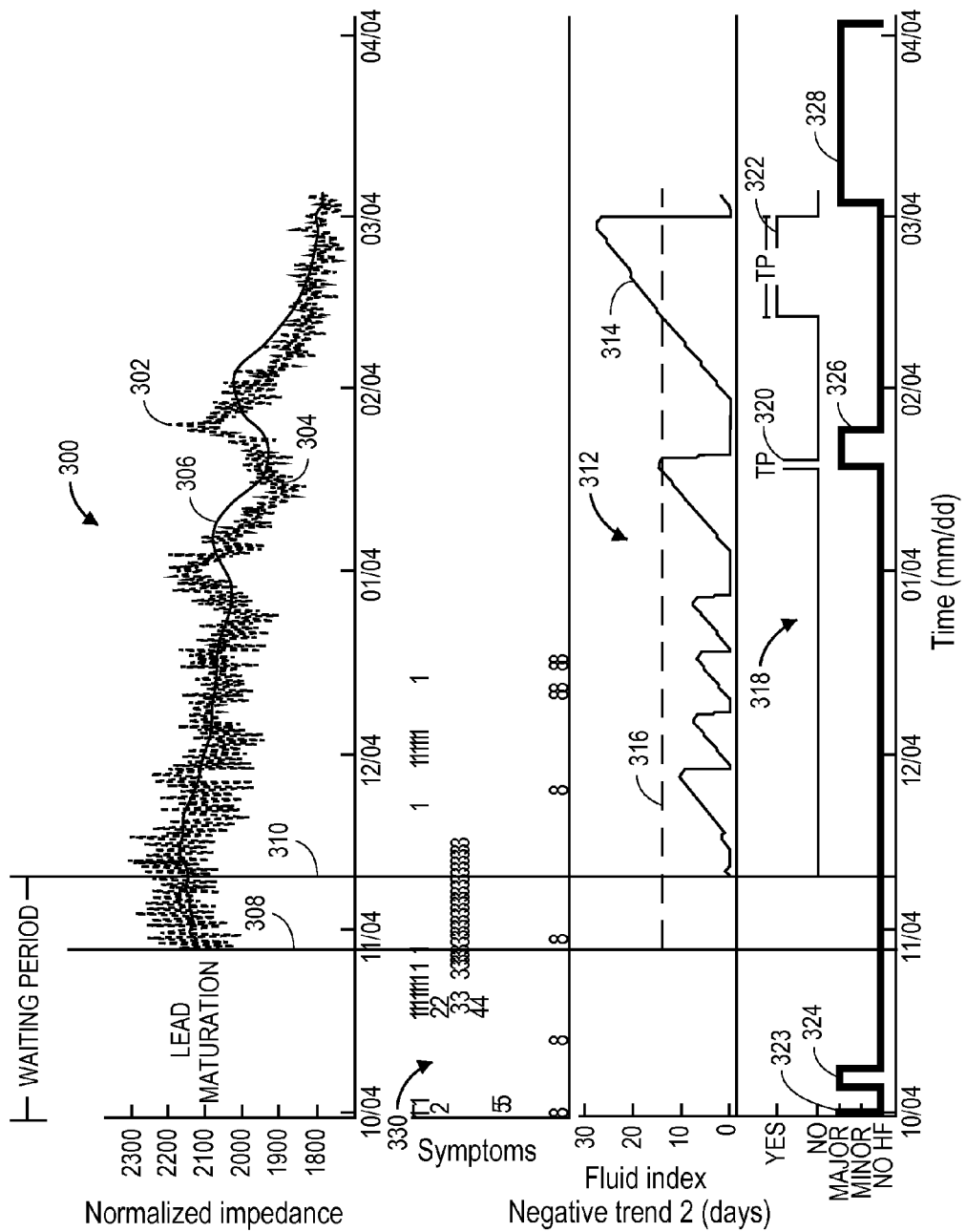
FIG. 5 includes graphs illustrating variations in transthoracic impedance and in an accumulated PE index, wherein no data is collected during lead maturation in accordance with predecessor techniques, and where PE events therefore cannot be detected during the interval.
Figure 6:
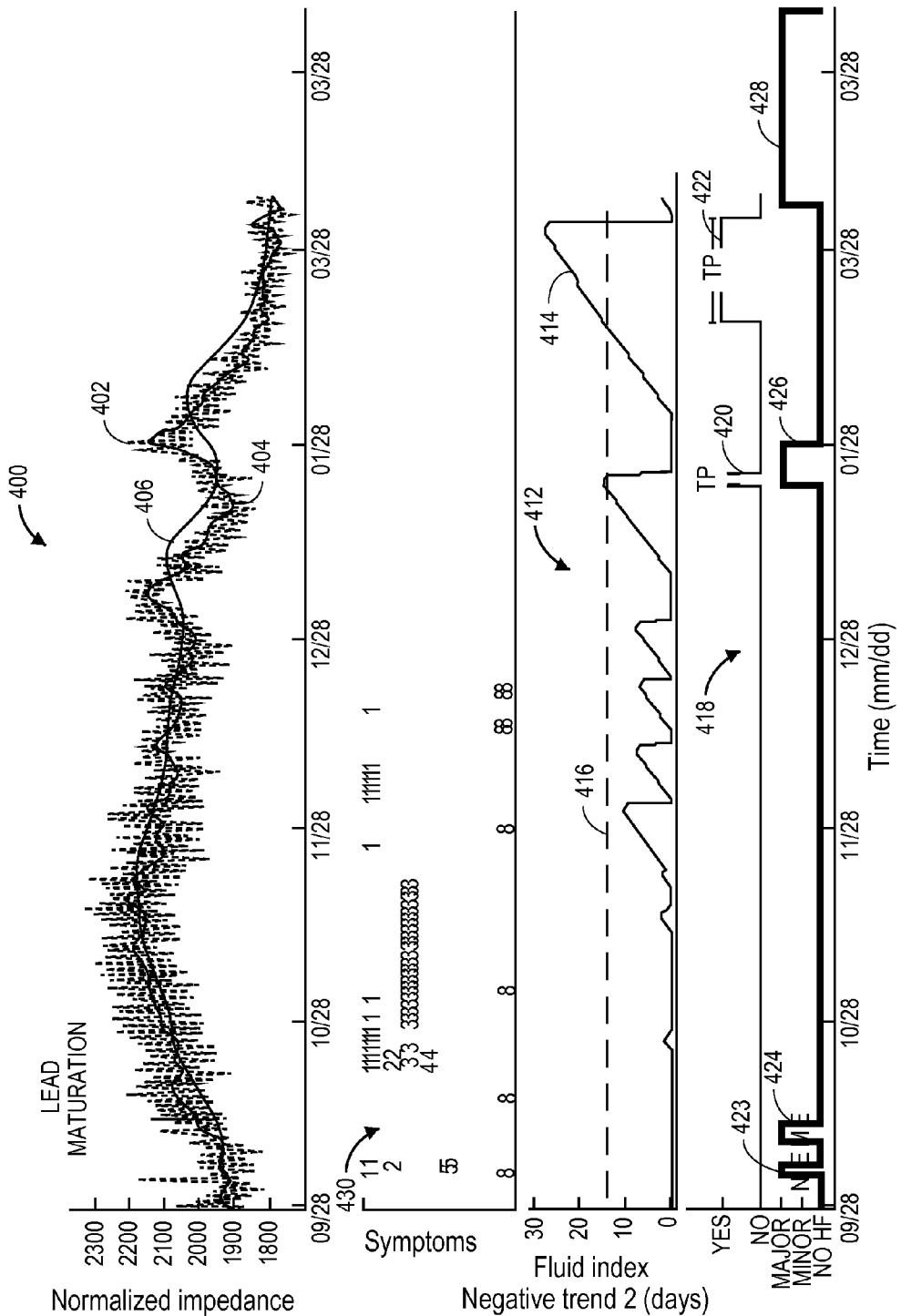
FIG. 6 includes graphs illustrating variations in transthoracic impedance and the PE index, wherein data is collected during lead maturation, but where neither the long-term averaging window nor the PE threshold are adjusted, such that PE events are again not properly detected during the interval.
Figure 7:
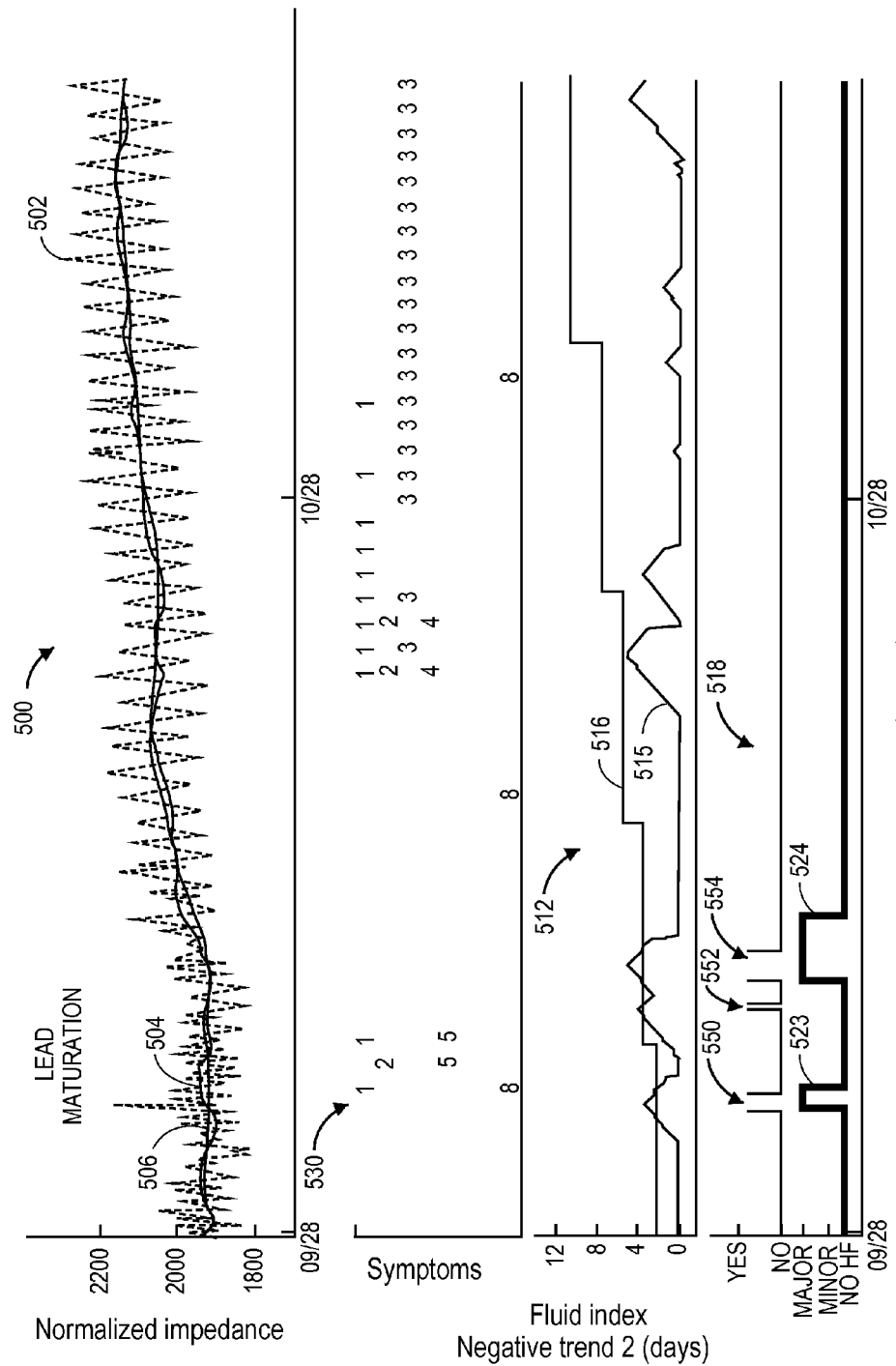
FIG. 7 includes graphs illustrating variations in transthoracic impedance and the PE index, wherein data is collected during the lead maturation period and wherein the long-term averaging window and the PE threshold are adjusted using the techniques of FIGS. 2-4, such that PE events can be reliably detected during lead maturation.

Turning now to FIGS. 5-7, various PE detection examples are illustrated, including examples that exploit the techniques of FIGS. 2-4 to detect PE during the post-implant interval, as well as examples that do not use these improvements.

FIG. 5 illustrates the use an initial waiting period and the blanking of initial impedance signals due to lead maturation, as performed by the predecessor devices discussed above. A first graph 300 illustrates normalized transthoracic impedance 302, a short-term average 304 and a long-term average 306, calculated using the "standard" window durations. That is, the short-term window duration is two days; the long-term window duration is fourteen days. [It should be understood that here, and throughout this document, these are merely exemplary values.] In this particular example, the CRT-D was implanted into the patient on or about September 28 (though the graph itself begins on October 4). However, in this example, the first month worth of impedance data is blanked (in accordance with predecessor techniques) such that tracking of impedance does not begin until about November 4 (as noted by vertical line 308.) No attempt is made to perform PE detection until about two weeks later (as noted by vertical line 310.) That is, no PE detection is attempted until the first long-term average can be completed based on two weeks of "non-blanked" impedance data. The interval from time 308 until 310 represents the long-term window duration. The interval from device implant until time 310 (when PE monitoring begins) represents the aforementioned waiting period.

A graph 312 illustrates the resulting PE detection index 314 (derived from short- and long-term averages), as well as a fixed PE detection threshold 316. Here, the threshold is set to a value of about 15 units. Another graph 318 illustrates a pair of PE detection events 320 and 324. (These are denoted TP, which stands for True Positive.) Graph 318 also illustrates actual PE episodes 323, 324, 326 and 328 known to have occurred in this patient. As can be seen, the technique fails to detect the initial PE events (323 and 324) since the events occur during the waiting period following device implant.

A graph 330 is also provided that identifies symptoms recorded for the patient. In this example, 1=tired, 2=short of breath, 3=extra pillows used (typically used in response to increasing pulmonary congestion), 4=awakened; 5=night cough; 6=pedal edema (i.e. swelling of the feet and legs), 7=extra pill taken by patient (typically a diuretic pill), and 8=patient called doctor. As can be seen, numerous symptoms or events were observed during the initial waiting period, perhaps in response to the initial heart failure exacerbation events.

Note that, although FIG. 5 illustrates certain predecessor PE detection techniques (including the use of a waiting period), the figure is not labeled as "prior art" since the figure illustrates a combination of elements, the entire combination of which is not necessarily admitted to be in the prior art.

FIG. 6 illustrates the use an initial waiting period without the blanking of initial impedance signals due to lead maturation. A first graph 400 illustrates normalized transthoracic impedance 402, a short-term average 404 and a long-term average 406, once again calculated using the "standard" window durations. As with the example of FIG. 5, the CRT-D of FIG. 6 was implanted on or about September 28. However, in this example, the first month worth of impedance data is not blanked. Instead, tracking of impedance begins immediately following implant.

A graph 412 illustrates the resulting PE detection index 414 (derived from short- and long-term averages obtained using the standard window durations), as well as a fixed PE detection threshold 416. Again, the detection threshold is set to a fixed value of about 15 units. Graph 418 illustrates a pair of PE detection events 420 and 424. Graph 418 also illustrates actual PE episodes 423, 424, 426 and 428 known to have occurred in the patient. As can be seen, the technique again fails to detect the initial PE events (423 and 424), even though impedance is now being detected during lead maturation.

The problem here is that the technique is still using the standard detection parameters (e.g. the standard long-term window duration and the standard detection threshold) and so the PE index 414 is too low during lead maturation to detect the PE events.

For the sake of completeness, FIG. 6 also provides a graph 430 identifying symptoms recorded for the patient.

FIG. 7 illustrates data collecting using the technique of FIGS. 3-4 wherein there is no blanking of impedance signals and wherein adjusted detection parameters are employed during the initial post-implant interval. Again, a first graph 500 illustrates normalized transthoracic impedance 502, a short-term average 504 and a long-term average 506, this time calculated using adjusted long-term window durations (as shown in FIG. 4.) As with the previous examples, the CRT-D was implanted on or about September 28. Note that, in this example, only data from implant until about six weeks after implant is illustrated. That is, the graph only illustrates data within the post-implant interval, during which the detection parameters are adjusted. This is so as to more clearly show the adjustments, particularly the adjustments made to the detection threshold.

A graph 512 illustrates the resulting PE detection index 514 (derived using adjusted long-term averages), as well as an increasing PE detection threshold 516. The threshold begins at about 2.5 units and then increases periodically, in steps. In this example, the detection threshold increases in steps where each step is greater in magnitude than previous steps. Although not shown in graph 512, the threshold ultimately reaches the standard threshold level of 15 units following a final increase at the end of the post-implant interval.

Graph 518 illustrates actual PE episodes 523 and 524 known to have occurred in the patient following device implant. Graph 518 also illustrates corresponding PE detection events 550, 552 and 554 (where event 552 slightly precedes actual event 524.) Note that, since events 552 and 554 are close to each other, these are considered a single detection event (which corresponds to actual event 524.) Note also that it is advantageous that the detection of an event occur prior to the actual onset of the event. For example, detection event 550 slightly precedes actual event 523.

Thus, as can be seen, the technique adequately detects the PE events (523 and 524), even though impedance is varying due to lead maturation. Although not shown, the technique also detects subsequent PE events (such events 326 and 328 of FIG. 5) occurring after the post-implant interval. These events are detected using the standard PE detection parameters.

Again, for the sake of completeness, FIG. 7 also provides a graph 530 identifying symptoms recorded for the patient. The initial group of recorded symptoms is likely correlated with the initial PE events.

What have been described are various techniques for detecting PE and related cardiopulmonary conditions within a patient. A detailed description of an exemplary CRT-D for implementing these techniques will now be provided. However, principles of invention may be implemented within other CRT-D implementations or within other implantable devices such as stand-alone monitoring devices, CRT devices or CRT-D devices.

Furthermore, although examples described herein involve processing of impedance data by the implanted device itself, some operations might be performed using an external device, such as a bedside monitor, device programmer, computer server or other external system such as the aforementioned Merlin systems. For example, recorded impedance data could be transmitted to an external device, which then processes the data to detect prior episodes of PE. Processing by the implanted device itself is preferred as that allows the device to promptly detect PE and to issue immediate warnings, control therapy, etc.

Exemplary CRT-D

Figure 8:
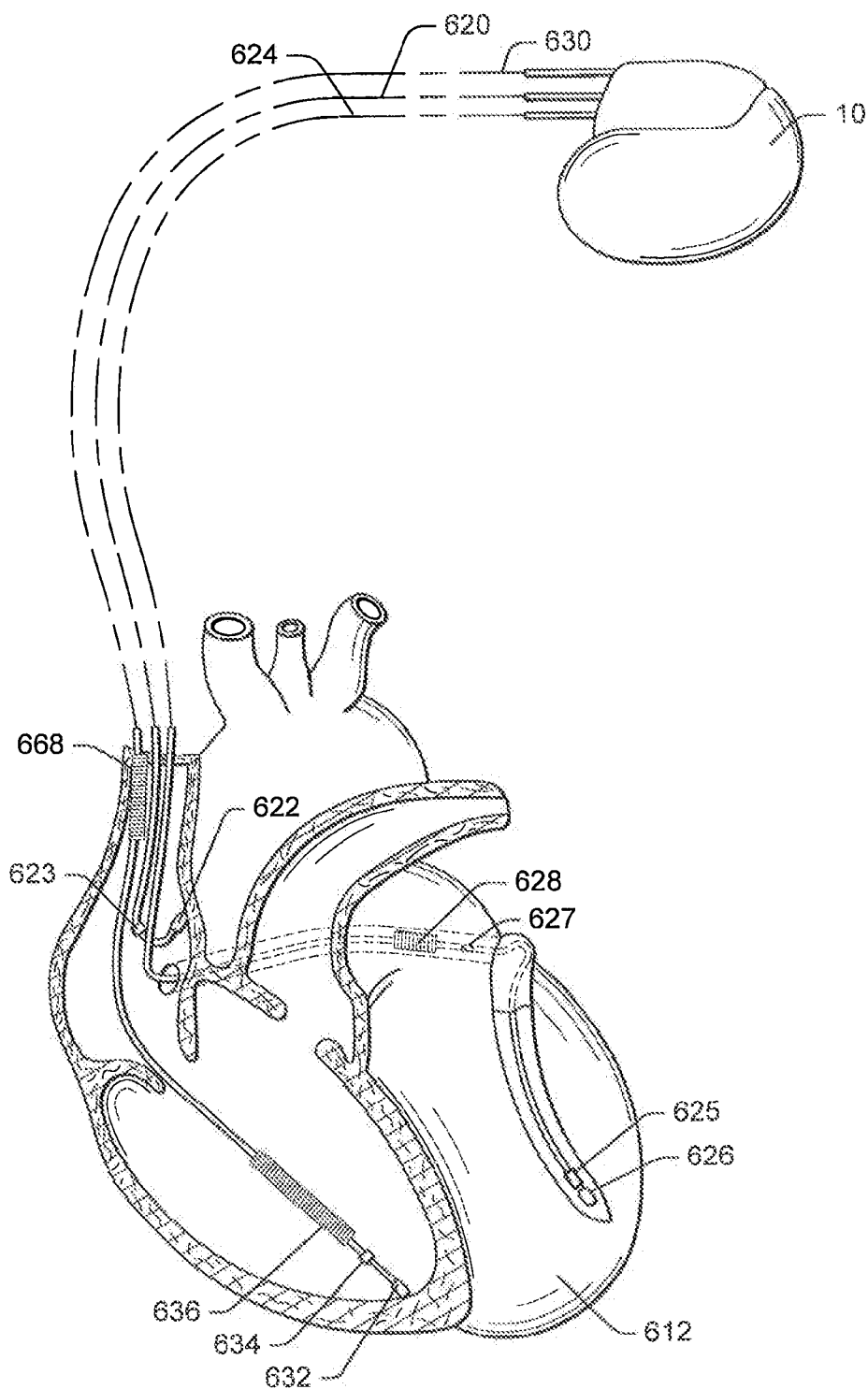
FIG. 8 is a simplified, partly cutaway view, illustrating the CRT-D of FIG. 1 along with at set of leads implanted into the heart of the patient.

FIG. 8 provides a simplified block diagram of the CRT-D, which is a dual-chamber stimulation device capable of treating both fast and slow arrhythmias with stimulation therapy, including cardioversion, defibrillation, and pacing stimulation, as well as capable of performing the force-frequency functions described above. To provide atrial chamber pacing stimulation and sensing, CRT-D 10 is shown in electrical communication with a heart 612 by way of a left atrial lead 620 having an atrial tip electrode 622 and an atrial ring electrode 623 implanted in the atrial appendage. CRT-D 10 is also in electrical communication with the heart by way of a right ventricular lead 630 having, in this embodiment, a ventricular tip electrode 632, a right ventricular ring electrode 634, a right ventricular (RV) coil electrode 636, and a superior vena cave (SVC) coil electrode 638. Typically, the right ventricular lead 630 is transvenously inserted into the heart so as to place the RV coil electrode 636 in the right ventricular apex, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, CRT-D 10 is coupled to a "coronary sinus" lead 624 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 624 is designed to receive atrial and ventricular cardiac signals and to deliver left ventricular pacing therapy using at least a left ventricular tip electrode 626, left atrial pacing therapy using at least a left atrial ring electrode 627, and shocking therapy using at least a left atrial coil electrode 628. With this configuration, biventricular pacing can be performed. Although only three leads are shown in FIG. 8, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 9:
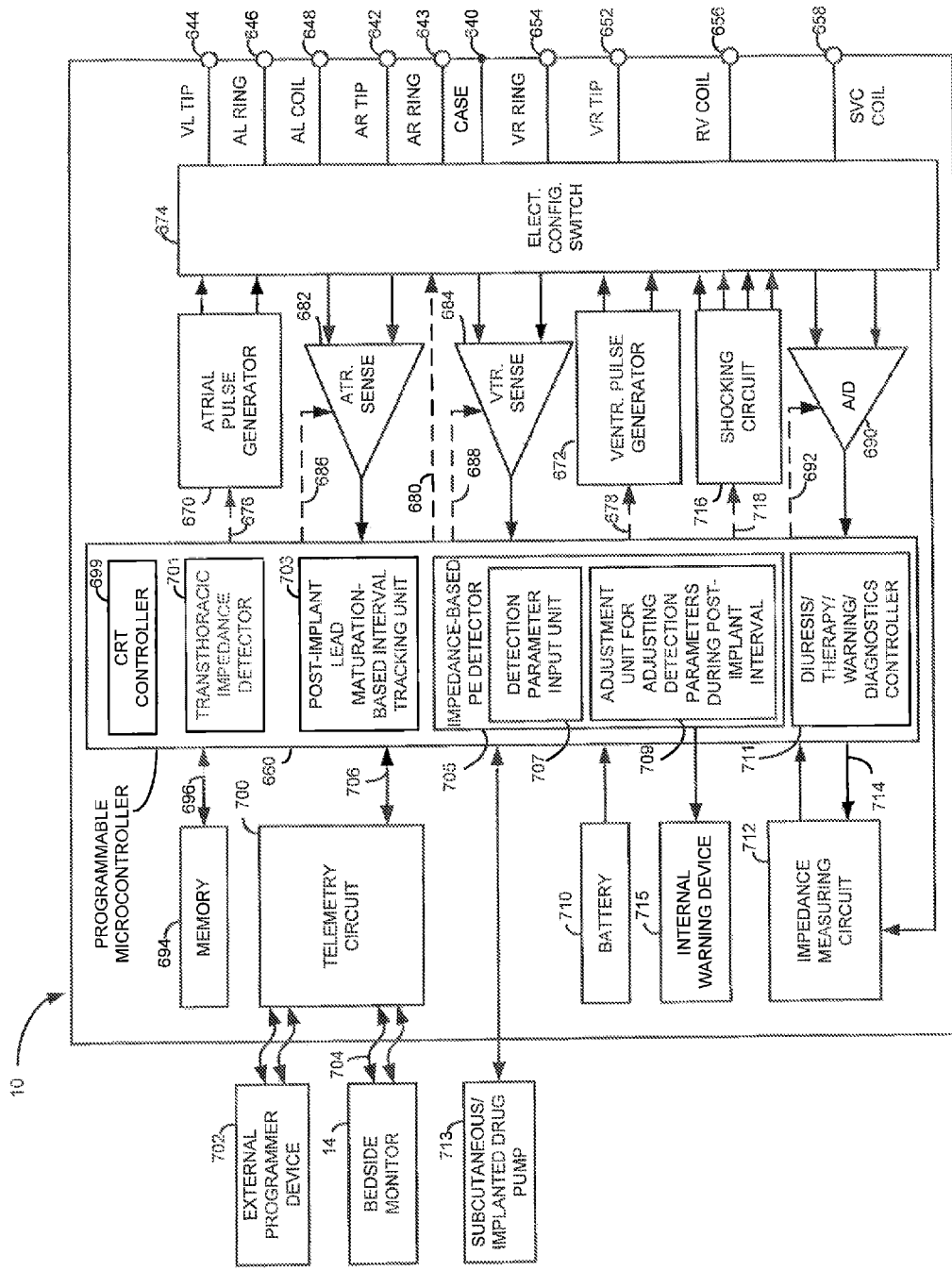
FIG. 9 is a functional block diagram of the CRT-D of FIG. 1, illustrating basic circuit elements that provide cardioversion, defibrillation and/or pacing stimulation in the heart and particularly illustrating components for monitoring PE using the techniques of FIGS. 2-4 and 7.

A simplified block diagram of internal components of CRT-D 10 is shown in FIG. 9. While a particular CRT-D is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned diastolic function monitoring functions.

The housing 640 for CRT-D 10, shown schematically in FIG. 9, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 643, 644, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 623. To achieve left chamber sensing, pacing and shocking, the connector includes at least a left ventricular tip terminal ($V_L$ TIP) 644, a left atrial ring terminal ($A_L$ RING) 646, and a left atrial shocking terminal ($A_L$ COIL) 648, which are adapted for connection to the left ventricular ring electrode 626, the left atrial tip electrode 627, and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal ($R_V$ COIL) 656, and an SVC shocking terminal (SVC COIL) 658, which are adapted for connection to the right ventricular tip electrode 632, right ventricular ring electrode 634, the RV coil electrode 636, and the SVC coil electrode 638, respectively.

At the core of CRT-D 10 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 9, an atrial pulse generator 670 and a Ventricular/impedance pulse generator 672 generate pacing stimulation pulses for delivery by the right atrial lead 620, the right ventricular lead 630, and/or the coronary sinus lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art.

Atrial sensing circuits 682 and ventricular sensing circuits 684 may also be selectively coupled to the right atrial lead 620, coronary sinus lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables CRT-D 10 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, CRT-D 10 utilizes the atrial and ventricular sensing circuits, 682 and 684, to sense cardiac signals to determine whether a rhythm is physiologic or pathologic. As used within this section, "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 690. The data acquisition system 690 is configured to acquire intracardiac electrogram signals, convert the raw analog data into a digital signal, and store the digital signals for later processing and/or telemetric transmission to an external device 702. The data acquisition system 690 is coupled to the right atrial lead 620, the coronary sinus lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of CRT-D 10 to suit the needs of a particular patient. Such operating parameters define, for example, the aforementioned thresholds as well as pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable CRT-D 10 may be non-invasively programmed into the memory 694 through a telemetry circuit 700 in telemetric communication with the external device 702, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of CRT-D 10 (as contained in the microcontroller 660 or memory 694) to be sent to the external device 702 through an established communication link 704. CRT-D 10 further includes an accelerometer or other physiologic sensor 708, commonly referred to as a "rate-responsive" sensor because it is typically used to adjust pacing stimulation rate according to the exercise state of the patient. However, the physiological sensor 708 may further be used to detect changes in cardiac output, changes in the physiological condition of the heart, or diurnal changes in activity (e.g., detecting sleep and wake states) and to detect arousal from sleep. Accordingly, the microcontroller 660 responds by adjusting the various pacing parameters (such as rate, AV Delay, V-V Delay, etc.) at which the atrial and ventricular pulse generators, 670 and 672, generate stimulation pulses. While shown as being included within CRT-D 10, it is to be understood that the physiologic sensor 708 may also be external to CRT-D 10, yet still be implanted within or carried by the patient. A common type of rate responsive sensor is an activity sensor incorporating an accelerometer or a piezoelectric crystal, which is mounted within the housing 640 of CRT-D 10. Other types of physiologic sensors are also known, for example, sensors that sense the oxygen content of blood, respiration rate and/or minute ventilation, pH of blood, ventricular gradient, etc.

The CRT-D additionally includes a battery 710, which provides operating power to all of the circuits shown in FIG. 9. The battery 710 may vary depending on the capabilities of CRT-D 10. If the system only provides low voltage therapy, a lithium iodine or lithium copper fluoride cell may be utilized. For CRT-D 10, which employs shocking therapy, the battery 710 must be capable of operating at low current drains for long periods, and then be capable of providing high-current pulses (for capacitor charging) when the patient requires a shock pulse. The battery 710 should also have a predictable discharge characteristic so that elective replacement time can be detected. Accordingly, CRT-D 10 is preferably capable of high voltage therapy and appropriate batteries.

As further shown in FIG. 9, CRT-D 10 is shown as having an impedance measuring circuit 712 which is enabled by the microcontroller 660 via a control signal 714. Uses for an impedance measuring circuit include, but are not limited to: detecting signals from which transthoracic impedance can be derived for use in detecting PE; lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 712 is advantageously coupled to the switch 674 so that any desired electrode may be used.

In the case where CRT-D 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 660 further controls a shocking circuit 716 by way of a control signal 718. The shocking circuit 716 generates shocking pulses of low (up to 0.5 joules), moderate (0.5-10 joules) or high energy (11 to 40 joules), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 660 is capable of controlling the synchronous or asynchronous delivery of the shocking pulses.

Microcontroller 660 includes a CRT controller 699 operative to control CRT functions. Microcontroller 660 also includes various components directed to detecting PE or related cardiopulmonary conditions. In particular, the microcontroller includes a transthoracic impedance detector 701 operative to derive transthoracic impedance from the impedance signals detected by circuit 712. A post-implant lead maturation-based interval tracking unit 703 is operative to determine the duration of the post-implant interval during which PE detection parameters are adjusted. The microcontroller also includes an impedance-based PE detector 705 operative to detect PE within the patient during the initial post-implant interval based on transthoracic impedance (using an adjusted set of detection parameters for use within the post-implant interval) and to further detect PE following the post-implant interval (using a set of non-adjusted detection parameters.) To this end, PE detector 705 includes a detection parameter input unit 707 operative to input or retrieve a set of standard PE detection parameters for use following the post-implant interval. These may be retrieved from memory 694 or may be input from an external programmer 702. PE detector 705 includes an adjustment unit 709 for adjusting the detection parameters for use during the post-implant interval, as described above.

Additionally, the microcontroller includes a diuresis/warning/therapy/diagnostics controller 711 for controlling at least some of these functions in response to the detection of PE or other conditions. In implementations where an implantable drug pump 713 is included, controller 711 controls the delivery of medications via the drug pump. Diagnostic data is stored within memory 694. Warning signals may be provided to the patient via an internal warning device 715 or via bedside monitor 14 or programmer 702. As noted above, a PAM may also be used.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller.

What have been described are various systems and methods for use with a CRT-D or an external system used in conjunction with a CRT-D. However, principles of the invention may be exploiting using other implantable medical systems. Thus, while the invention has been described with reference to particular exemplary embodiments, modifications can be made thereto without departing from the scope of the invention.

What is claimed is:

1. A system for use with an implantable medical device for implant within a patient along with at least one lead, the system comprising:
   a post-implant interval tracking unit operative to determine whether the lead is within an initial post-implant lead maturation-based interval following lead implant, wherein the post-implant interval tracking unit is configured to:
      set the initial post-implant lead maturation-based interval equal to a lead maturation period plus a long-term average window duration, and
      track an amount of time since lead implant to determine whether the lead is within the initial post-implant interval;
   a transthoracic impedance detector operative to detect values representative of transthoracic impedance; and
   an impedance-based medical condition detector operative to detect a medical condition within the patient during the initial post-implant interval based on transthoracic impedance using a set of detection parameters for use within the post-implant interval.

2. The system of claim 1 wherein the detection unit is further operative to detect a medical condition within the patient following the post-implant interval based on transthoracic impedance using a set of detection parameters that differ from those used during the post-implant interval.

3. The system of claim 1 wherein the implantable medical device is equipped to deliver cardiac resynchronization therapy (CRT).

4. The system of claim 1 further comprising an adjustment unit operative to adjust the detection parameters based on the amount of time since implant.

5. The system of claim 4, wherein the detection parameters comprise at least one of the long-term window duration and a PE threshold.

6. The system of claim 4 further comprising a detection parameter input unit operative to input or retrieve one or more initial detection parameters, wherein the detection parameters comprise the long-term window, and wherein the adjustment unit is operative to adjust the duration of the long-term window to a proper fraction of the initial long-term window value based on the amount of time since lead implant and the post-implant interval.

7. The system of claim 4 further comprising a detection parameter input unit operative to input or retrieve one or more initial detection parameters, wherein the detection parameters comprise the long-term window, and wherein the adjustment unit is operative to adjust the duration of the long-term window based on a linear adjustment function.

8. The system of claim 4 further comprising a detection parameter input unit operative to input or retrieve one or more initial detection parameters, wherein the detection parameters comprise the long-term window, and wherein the adjustment unit is operative to adjust the duration of the long-term window based on a non-linear adjustment function.

9. The system of claim 4, wherein the detection parameters comprise a PE detection threshold, and wherein the adjustment unit is operative to adjust the threshold to a proper fraction of a standard value based on the amount of time since lead implant and the post-implant interval.

10. The system of claim 4, wherein the detection parameters comprise a PE detection threshold, and wherein the adjustment unit is operative to adjust the duration of the PE detection threshold based on a linear adjustment function.

11. The system of claim 4, wherein the detection parameters comprise a PE detection threshold, and wherein the adjustment unit is operative to adjust the duration of the PE detection threshold based on a non-linear adjustment function.

12. The system of claim 4 further comprising a detection parameter input unit operative to input or retrieve an initial long-term window, wherein the adjustment unit is operative to:
adjust the duration of the long-term window to a proper fraction of the initial long-term window value based on the amount of time since lead implant and the post-implant interval,
adjust the duration of the long-term window based on a linear adjustment function, or
adjust the duration of the long-term window based on a non-linear adjustment function.

13. The system of claim 12 wherein the adjustment unit is further operative to:
determine whether the long-term average is greater than the short-term average; and
when the long-term average is greater than the short-term average, increase a PE detection index.

14. The system of claim 13 wherein the transthoracic impedance detector is operative to compare the PE detection index to a current value for the PE detection threshold to detect edema.

15. The system of claim 1 further comprising an implantable drug pump and a controller operable to control the delivery of medications via the drug pump.

16. The system of claim 1 further comprising the implantable medical device, wherein the implantable medical device is external to the transthoracic impedance detector.

17. The system of claim 1 further comprising a detection parameter input unit operative to input or retrieve an initial long-term window, wherein the adjustment unit is operative to:
adjust the duration of the long-term window to a proper fraction of the initial long-term window value based on the amount of time since lead implant and the post-implant interval,
adjust the duration of the long-term window based on a linear adjustment function, or
adjust the duration of the long-term window based on a non-linear adjustment function.

18. The system of claim 17 wherein the adjustment unit is further operative to:
determine whether the long-term average is greater than the short-term average; and
when the long-term average is greater than the short-term average, increase a PE detection index.

19. The system of claim 18 wherein the transthoracic impedance detector is operative to compare the PE detection index to a current value for the PE detection threshold to detect edema.

20. A system for use with an implantable medical device for implant within a patient along with at least one lead, the system comprising:
means for determining whether the lead is within an initial post-implant lead maturation-based interval following lead implant, configured to:
set the initial post-implant lead maturation-based interval equal to a lead maturation period plus a long-term average window duration, and
track an amount of time since lead implant to determine whether the lead is within the initial post-implant interval;
means for detecting values representative of transthoracic impedance within the patient;
means for detecting a medical condition within the patient during the initial post-implant interval based on transthoracic impedance using a set of detection parameters for use within the post-implant interval; and
means for detecting a medical condition within the patient following the initial post-implant interval based on transthoracic impedance using a set of detection parameters that differ from those used during the post-implant interval.

* * * * *